United States Patent [19]

Vora

[11] 4,367,357

[45] Jan. 4, 1983

[54] PROCESS FOR THE CONVERSION OF BUTANES INTO GASOLINE

[75] Inventor: Bipin V. Vora, Elk Grove Village, Ill.

[73] Assignee: UOP Inc., Des Plaines, Ill.

[21] Appl. No.: 272,404

[22] Filed: Jun. 10, 1981

Related U.S. Application Data

[63] Continuation-in-part of Ser. No. 101,329, Dec. 6, 1979, abandoned.

[51] Int. Cl.³ .............................................. C07C 3/54
[52] U.S. Cl. .................................... 585/332; 585/314; 585/315; 585/331; 585/723
[58] Field of Search ............... 585/314, 315, 331, 332, 585/723

[56] References Cited

U.S. PATENT DOCUMENTS

| | | | |
|---|---|---|---|
| 2,314,435 | 3/1943 | Allender | 585/315 |
| 2,389,984 | 11/1945 | Jones | 585/303 |
| 3,409,540 | 11/1968 | Gould et al. | 208/79 |
| 3,904,384 | 9/1975 | Kemp et al. | 44/56 |
| 3,931,352 | 1/1976 | Mikulicz | 585/332 |

*Primary Examiner*—Curtis R. Davis
*Attorney, Agent, or Firm*—James R. Hoatson, Jr.; John F. Spears, Jr.; William H. Page, II

[57] ABSTRACT

An improved multiconversion zone process which results in an increased yield of motor fuel blending stocks from butanes is disclosed. A butane mixture is fractionated into isobutane-rich and normal butane-rich process streams, with the normal butane-rich stream being passed into an isomerization zone. All of the $C_4$'s in the isomerization zone effluent and the normal butane-rich process stream are passed through a dehydrogenation zone. The entire dehydrogenation zone effluent stream is passed into an alkylation zone, and the alkylation zone effluent is fractionated. An alkylate-containing normal butane stream is recycled to the feed fractionator, and alkylate from the feed fractionator is admixed with an alkylate stream from the alkylation zone product fractionator to produce a product stream.

11 Claims, 1 Drawing Figure

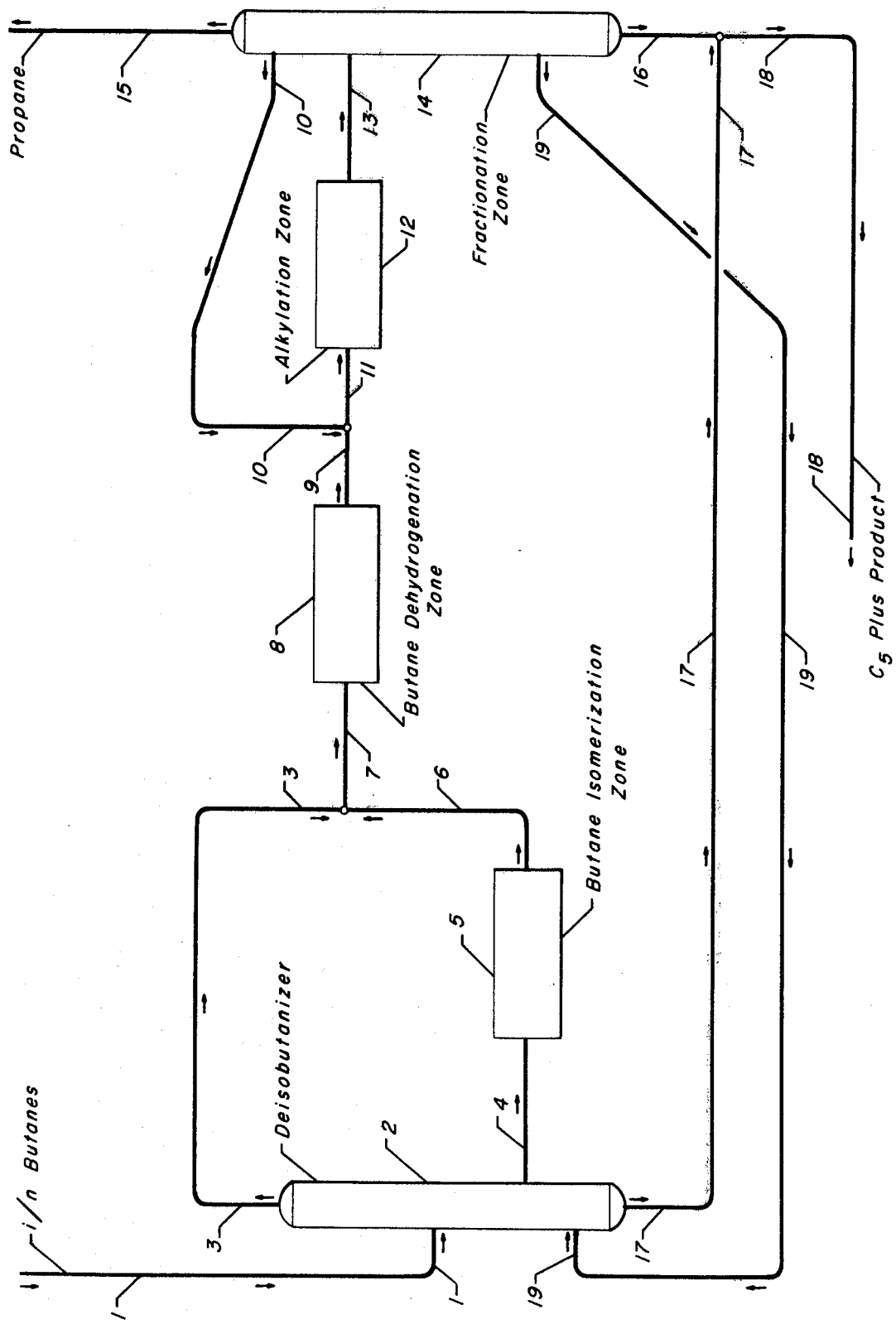

PROCESS FOR THE CONVERSION OF BUTANES INTO GASOLINE

CROSS REFERENCE TO RELATED APPLICATION

This application is a continuation-in-part of my prior copending application Ser. No. 101,329 filed Dec. 6, 1979 and now abandoned. The teaching and disclosure of my prior application is hereby incorporated by reference.

FIELD OF THE INVENTION

The invention is a multi-step hydrocarbon conversion process which involves the isomerization of butanes, the dehydrogenation of butanes and the alkylation of $C_4$ hydrocarbons. Processes of this nature are often classified in Classes 260 and 208. The invention is directly related to a process for the production of a $C_8$ gasoline blending stock from saturate $C_4$ hydrocarbons.

PRIOR ART

The production of motor fuel by the alkylation of light paraffins with $C_3$ and/or $C_4$ olefins is a widely practiced commercial process. Liquid phase hydrofluoric acid (HF) is often employed as the catalyst. This process is well described in the literature and the integration of HF alkylation with other processes such as dehydrogenation is well known to those skilled in the art.

Processes for the isomerization of normal paraffins and for the dehydrogenation of paraffins are also well described in the available literature. This description includes a listing of process flows, process conditions and catalysts which may be employed in these processes.

Integrated processes in which these three individual processing steps, and sometimes others, are used to produce motor fuel blending components are also well known. For instance, a multi-step process in which nornal butanes are isomerized and the resultant isobutane is consumed in an alkylation zone by reaction with olefinic hydrocarbons is described in U.S. Pat. No. 3,931,352. U.S. Pat. No. 3,409,540 also illustrates the sequential steps of butane isomerization and alkylation. U.S. Pat. No. 3,904,384 describes a multi-step process in which gasoline blending components are produced from normal butane and isobutane. The process includes the steps of fractionation, normal butane isomerization, thermal dehydrogenation of the isobutane and etheration of the isobutylene with isopropanol which is also produced in the process.

U.S. Pat. Nos. 2,314,435 and 2,389,984 are believed to be the most pertinent of integrated processes. In the former a feed stream of mixed butanes and other streams enter a fractionation zone and are separated into a normal butane stream, an isobutane stream and an alkylate product stream. One portion of the normal butane is passed through an isomerization zone and returned to the fractionation zone and a second portion of the normal butane is passed into a dehydrogenation zone. All of the isobutane stream and the $C_4$ fraction of the dehydrogenation zone effluent are passed into an alkylation zone. The effluent of the alkylation zone is passed into the initial fractionation zone. In the latter reference several alternative process flows are described. A feed stream of mixed butanes are passed into a feed fractionation zone and isobutanes and normal butanes are separated. The normal butanes are split between a dehydrogenation zone and an isomerization zone. The effluent stream of the isomerization zone is recycled to the feed fractionation zone. The effluent stream of the dehydrogenation zone may be pased into a polymerization zone or an alkylation zone or both. The isobutanes are passed directly into the alkylation zone, although a portion of the isobutanes may be passed into a second dehydrogenation zone to produce isobutenes which are charged to the polymerization zone. The effluent of the alkylation zone is passed into a second or product fractionation zone, with a single mixed butane stream being separated out for passage to one of these areas: the alkylation zone, the feed fractionation zone or a separate butane splitter column operated in parallel to the feed fractionation zone.

In both of these references the isomerization zone effluent stream is recycled to the feed fractionation zone rather than being passed into another process zone. Also, in neither of these references is an isobutane-rich stream passed into a dehydrogenation zone to produce isobutylenes for comsumption in an alkylation zone. The butane-alkylate fractionation method of the subject process is believed also not disclosed in these references.

BRIEF SUMMARY OF THE INVENTION

The invention provides an improved process for producing $C_8$ gasoline blending components from a mixture of isobutane and normal butane. The process offers the advantages of low capital costs, lower utility costs and greater product yield than prior art systems. A broad embodiment of the inventive concept may be characterized as a hydrocarbon conversion process which comprises the steps of separating a feed stream which comprises a mixture of isobutane and normal butane into a first process stream which is rich in normal butane and a second process stream which is rich in isobutane in a first fractionation column, with the first process stream being withdrawn from the first fractionation zone at a first intermediate point; passing the first process stream through an isomerization zone and thereby producing an isomerization zone effluent stream which comprises a mixture of isobutane and normal butane; passing the entire butane isomerization zone effluent stream and the second processs stream, which if combined would contain less than 40 mole percent normal butane, through a dehydrogenation zone and thereby producing a dehydrogenation zone effluent stream which comprises normal butane, isobutane, normal butenes and isobutylene; passing the dehydrogenation zone effluent stream into an alkylation zone and thereby effecting the production of an alkylation zone effluent stream which comprises normal butane, isobutane, isopentane and $C_8$ branched-chain hydrocarbons; separating the alkylation zone effluent stream in a second fractionation zone and thereby producing a first bottoms stream which is rich in $C_8$ branched-chain hydrocarbons and a lower sidecut stream which is rich in normal butane and comprises $C_8$ branched-chain hydrocarbons; passing the lower sidecut stream into the first fractionation zone at a lower second intermediate point; withdrawing a second bottoms stream comprising $C_8$ branched-chain hydrocarbons from the first fractionation zone; and combining the first and the second bottoms streams and producing a product stream which is rich in $C_8$ branched-chain hydrocarbons.

DESCRIPTION OF THE DRAWING

The Drawing illustrates one embodiment of the invention. This is not intended to remove from the inventive concept those other embodiments set out herein or which result from variations of these embodiments. Minor auxiliary flows such as makeup hydrogen supplies and light ends removal streams and normal equipment such as pumps and valves are not shown.

Referring to the Drawing, a feed stream comprising a mixture of isobutane and normal butane enters the process through line 1 and is passed into a deisobutanizer column 2 at an upper intermediate point. The deisobutanizer is designed and operated to separate the butanes contained in the process streams fed to this column into a net overhead stream carried by line 3 which is rich in isobutane and a lower sidecut stream carried by line 4 which is rich in normal butane. The normal butane-rich stream of line 4 is passed into a butane isomerization zone 5 wherein a substantial portion of the normal butane in this stream is converted to isobutane. The butane isomerization zone may contain heaters, condensers, phase separation and fractionation vessels and hydrogen recycle facilities not shown on the Drawing.

The effluent stream of the butane isomerization zone is carried by line 6 and is admixed with the isobutane-rich stream carried by line 3. The resultant admixture preferably contains more than 70 mole percent isobutane and is passed through line 7 into a butane dehydrogenation zone 8. The butane dehydrogenation zone may also contain separation, fractionation and hydrogen recycle facilities as required. The net effluent stream of the butane dehydrogenation zone carried by line 9 comprises a mixture of normal butane, isobutane, normal butenes and isobutene. A recycle stream rich in isobutane carried by line 10 is admixed with the butane dehydrogenation zone effluent stream, and the resultant admixture is passed into the alkylation zone 12 through line 11. All of the hydrocarbons which enter the alkylation zone have therefore passed through the dehydrogenation zone at least once.

Within the alkylation zone the entering hydrocarbons are preferably contacted with liquid-phase HF under conditions which result in the reaction of the entering olefinic hydrocarbons with the isobutane. The effluent of the alkylation zone will contain $C_8$ branched-chain hydrocarbons and unreacted isobutane and normal butane. Essentially all of the olefins will be consumed in the reaction. The alkylation zone effluent is passed into a fractionation zone 14 through line 13. A stream rich in isobutane is removed from this fractionation zone in line 10 and passed into the alkylation zone. Line 10 recycles an isobutane-rich stream to the alkylation zone to provide a high isobutane to olefin ratio in the alkylation zone. If there is a buildup of isobutane in this loop, a portion of the isobutane may be passed into the deisobutanizer or isomerization zone after alumina treating.

A net overhead vapor stream comprising HF, isobutane and propane produced in the alkylation zone is removed from the fractionation zone through line 15. A lower sidecut stream is removed at a lower intermediate point from the fractionation zone 14 in line 19 and is passed into the deisobutanizer. This stream is rich in normal butane and contains lesser amounts of isobutane, isopentane and the product alkylate. This is the only normal butane recycle stream of the process. A net bottoms stream comprising most of the alkylate produced in the alkylation zone is removed from the fractionation zone in line 16. This stream is admixed with the net bottoms stream of the deisobutanizer carried by line 17, which contains normal butane and lesser amounts of isopentanes and $C_6$-plus hydrocarbons including some alkylate. The resultant $C_5$-plus admixture is removed in line 18 as the net product of the process.

DETAILED DESCRIPTION

Large amounts of light hydrocarbons which were previously flared at the well site are now being collected and processed. It is expected that in several geographical areas, this will lead to an imbalance between the supply and the demand for saturated butanes. It is an objective of this invention to provide a process for upgrading saturate butanes into a gasoline blending stock. Such a process can alleviate the local excess supply of butanes which is expected to arise in various European and Arabic locations. The subject process will also allow the excess butanes to be converted into normally liquid hydrocarbons which are easily transported in conventional liquid carrying transports.

The subject process has several distinguishing features and several advantages when compared to prior art integrated processes for converting butane to $C_8$ hydrocarbons such as previously cited U.S. Pat. Nos. 2,314,435 and 2,389,984. For instance, in the subject process an isobutane-rich stream is passed into the dehydrogenation zone. This seemingly small difference has a large impact on the performance of the overall process when compared to passing a normal butane-rich stream into the dehydrogenation zone. One very significant advantage, especially with the preferred catalyst, is a very real increase in the total $C_8$ yield of the process. This results from a tendency for there being less cracking to lighter by-products when isobutane is being dehydrogenated than when normal butane is being dehydrogenated. With 100 mole percent normal butane it is expected that the $C_3$-minus by-products produced in the dehydrogenation unit will be in excess of 20 mole percent of the feed and may reach 25 mole percent of the feed (based on total conversion). In comparison if the feed stream is pure isobutane the $C_3$-minus light ends make is expected to be less than 10 mole percent. This difference in by-product rates translates directly into a difference in available feed for alkylation and therefore has a major impact on the ultimate yield of $C_8$ product from the process.

A second advantage of the passage of an isobutane-rich stream into the dehydrogenation zone results from the lower rate of diolefin production which occurs when the feed butane to the dehydrogenation zone is isobutane. The rate of butadiene formation is lower for isobutane than for normal butane. A relatively high butadiene concentration in the feed stream to the alkylation unit results in a high rate of tar formation and a high rate of HF consumption when HF is used as the catalyst. These rates can become a very significant economic factor in the operation of the alkylation zone. The solution to this problem is the selective hydrogenation of the dehydrogenation zone effluent stream prior to its passage into the alkylation zone. The equipment and utilities cost of this required hydrogenation zone, which is not shown in the references, is considerable and would result in the overall process costing more to build and operate. In the subject process the dehydrogenation zone feed stream contains a large amount of isobutane, and the diolefin content of the dehydrogenation zone effluent stream therefore drops to a low level at which HF consumption is acceptable and selective hydrogenation is not required.

Thus, in comparison to the prior art, the subject process produces a greater product yield at a lower cost. To achieve this result the combined feed stream to the dehydrogenation zone should contail less than 40 mole percent normal butane. Preferably, this stream contains 70 mole percent or more isobutane. The highest feasible isobutane concentration is desired, and therefore concentrations of 75 or 80 mole percent isobutane would be desired.

It is believed that the performance characteristics ascribed above to the dehydrogenation zone are true for all catalytic butane dehydrogenation zones and are not dependent on the dehydrogenation catalyst employed. However, it is known that these results, as set out above, are observed with the preferred catalyst and in several minor variations of the preferred catalyst.

Another advantage of the subject process, which is not related to the operation or feed composition of the dehydrogenation zone, is that the total amount of material entering the first fractionation column is lower than in the cited prior art processes. These processes recycle the isomerization zone effluent to the first fractionation column. In the subject process the isomerization zone effluent stream is passed through both the dehydrogenation and alkylation zones and a considerable amount of the isomerization zone effluent stream is therefore first consumed rather than being recycled, fractionated and then consumed.

The feed stream to the subject process contains a mixture of isobutane and normal butane. Since this feed stream is expected to be derived from natural gas, the concentration of normal butane is expected to be several times greater than the concentration of isobutane. However, high normal butane contents are not preferred. It is preferred that over 95 mole percent of the feed stream is $C_4$ hydrocarbons. It is also preferred that the feed stream contains less than 1 mole percent $C_5$-plus hydrocarbons. Several mole percent of propane is acceptable. The feed stream is passed into a first fractionation zone, which preferably comprises a single trayed column referred to herein as the first fractionation column. As used herein, the term "fractionation zone" is intended to refer to the process equipment in which a specified separation is performed and may include one or more fractionation columns as desired. Fractionation zones also comprise such auxiliary equipment as reboilers, overhead vapor condensers and overhead receivers as may be required.

The first fractionation column is also referred to herein as the deisobutanizer or deisobutanizer column following the customary practice of referring to a column by its overhead product. It is the function of the deisobutanizer column to separate the $C_4$ components of the entering streams into a net overhead stream which is rich in isobutane and a lower sidecut stream which is rich in normal butane. It is preferred that the deisobutanizer overhead stream, also referred to herein as the second process stream, contains over 90 mole percent isobutane. A much smaller bottoms stream comprising some normal butane and heavier hydrocarbons such as pantenes, hexanes or octanes will also normally by withdrawn from the first fractionation column to prevent the buildup of these heavier materials. As used herein, the term "rich" is intended to indicate that a process stream contains at least 55 mole percent of the particular hydrocarbon which is specified. It is believed that in most cases, a column containing about 40 trays will be sufficient as the deisobutanizer when correctly designed and operated. A representative set of operating conditions includes an overhead vapor temperature of approximately 38° C. at a pressure of about 80 psig.

A second fractionation zone is also employed in the subject process. The alkylation zone effluent stream is passed into the first column of this zone, which preferably contains three distillation columns. The first column functions in a manner similar to the column normally referred to as the isostripper in HF alkylation units which produce motor fuel alkylate. A representative set of operating conditions for this column includes an overhead vapor temperature of about 60° C. and an overhead pressure of approximately 150 psig. It may contain about 65 actual trays. Preferably the alkylation zone effluent stream enters the first or isostripper column at an intermediate point. Sidecut streams are then removed above and below the feed point. The upper sidecut carries isobutane which has passed through the alkylation zone. Preferably, this isobutane-rich stream is recycled into the alkylation zone. The lower sidecut stream will be rich in normal butane and is recycled to the first fractionation zone to recycle the normal butane. Since it is a sidecut stream it will contain some product alkylate. A sidecut stream is by definition removed from an intermediate point in a fractionation column. As used herein the term "intermediate point" is used to indicate a point which is separated from the closest end of the column by at least two actual fractionation trays or an amount of packing equal to at least two theoretical trays.

Propane which is present in the feed stream to the process may enter the isostripper as part of the alkylation zone effluent stream. The propane is concentrated into the net overhead vapor of the isostripper. The overhead of the isostripper column will also contain HF and isobutane. This net overhead is preferably passed into a second column referred to in the art as a depropanizer in which the isobutane is recovered as a bottoms product. This isobutane is preferably recycled back to the alkylation zone by admixture into the upper sidecut stream of the isostripper. If there is an excess of isobutane in the alkylation unit, this bottoms stream is a good source of high purity isobutane and may be passed into the dehydrogenation zone after being alumina treated. The net overhead of the depropanizer comprises HF and propane and is preferably sent to a third column in which HF is stripped off as an overhead product. The HF may be returned to the alkylation zone and the propane is removed as a net bottoms product and transferred to suitable storage facilities after alumina treatment.

Most of the alkylate present in the net alkylation zone effluent stream is concentrated into a net isostripper bottoms stream and then admixed with the net bottoms stream of the first fractionation zone, which contains some normal butane but mostly $C_5$-plus hydrocarbons which enter the first fractionation column. Some normal butane is normally required to be admixed with the alkylate to increase its vapor pressure up to that specified for gasoline. However, if the net alkylate product is intended for lengthy storage or transportation, it may be advisable to minimize the butane content of the product and to thereby lessen vaporization losses. The butane can therefore be blended into the alkylate at a later time.

The normal butane-rich sidecut stream (first process stream) removed from the deisobutanizer is passed into a butane isomerization zone which comprises a reactor and auxiliary process equipment such as heaters, condensers, separatory vessels, etc. The isomerization zone also contains a stripping column which eliminates light ends (hydrogen, methane, ethane) from the net effluent of the isomerization zone. With the preferred catalyst, this stripping column will also remove volatile chloride compounds from the isomerization zone effluent. The core of the operation of this zone is passage of the sidecut stream through a reactor maintained at butane isomerization-promoting conditions including the presence of an acidic isomerization catalyst. This is normally a relatively low pressure operation performed at a pressure of from about 50 to 600 psig and at an elevated temperature as required by the activity of the catalyst. The average reactant temperature may be as high as 500° C., but is preferably between 100° and 320° C. It is normal practice to pass the butane through the reactor in admixture with between 1 and 10 moles of hydrogen per mole of butanes to ensure vapor phase conditions and to suppress coke deposition on the catalyst. It is preferred that the butane is passed vertically through one or more fixed beds of catalyst located within the reactor at a liquid hourly space velocity between 1.0 and 6.0, but space velocities in the broad range of 0.5 to 12.0 can be employed if desired. The effluent of the isomerization reactor is normally separated into a hydrogen-rich recycle gas which is returned to the reactor and an isomerate-containing liquid stream. It is within the scope of the inventive concept that this liquid stream may be fractionated to allow the recycling of normal butanes and the achievement of higher conversion rates, but this is not preferred. Further details on the butane isomerization step of the subject process may be obtained by referring to the previously cited references.

The preferred isomerization-promoting catalyst for use in the isomerization zone comprises a platinum group component and a halogen component supported by an inorganic oxide carrier. In general, the carrier material is a porous, high surface area material which is relatively refractory to the conditions utilized in the isomerization process. The carrier material may be selected from silica, alumina, titanium dioxide, chromium, or mixtures of these oxides; various naturally occurring refractory oxides in different degrees of purity, such as bauxite and bentonite clay; or a diatomaceous earth such as kieselguhr. Of the above-mentioned oxides, alumina is preferred and particularly preferred is a synthetically prepared substantially anhydrous gamma-alumina with a high degree of purity.

The preferred platinum group component is platinum, palladium or a mixture of platinum and palladium. This however is not intended to exclude the other platinum group metals such as rhodium, ruthenium, osmium and iridium. A platinum group component may exist within the final catalytic composite as an oxide, a sulfide or a halide, etc., or as an elemental metal. On a weight basis, the platinum group component will comprise only a minor fraction of the total catalytic material. The preferred catalyst will therefore contain less than about 2.0 wt.% of the platinum group component, with the preferred concentration being from about 0.05 to about 1.0 wt.%. The method by which the platinum group component is made part of the catalytic composite is not controlling. It may therefore be added by coprecipitation or cogelation with the preferred carrier material or by ion-exchange or impregnation on pre-existing carrier material. The preferred method of preparing the catalyst impregnates the carrier material by contacting it with an aqueous solution of a water-soluble, decomposable compound of a platinum group metal. This may be performed by dipping the carrier material in a solution of chloroplatinic acid, ammonium chloroplatinate, bromoplatinic acid, or platinum dichloride. The utilization of a platinum chloride compound is preferred since it facilitates the incorporation of both the platinum component and at least a minor quantity of the halogen component in a single step.

There are also numerous ways in which to add the halogen component to the isomerization catalyst. The halogen component may be composited with the carrier material during the impregnation of the carrier material with the platinum group component by the utilization of a mixture of chloroplatinic acid and hydrogen chloride. Altenatively, the alumina hydrosol which is typically utilized to form the preferred alumina carrier material may contain at least a portion of the halogen. The halogen may also be added by contacting a calcined carrier material with an aqueous solution of an acid such as hydrogen chloride, hydrogen fluoride, or hydrogen bromide, etc. The halogen component may be selected from chlorine, fluorine, iodine, bromine or mixtures thereof with chlorine and fluorine being particularly preferred. The halogen component is normally referred to as a combined halogen and is typically present in an amount of from 0.01 to about 5.0 wt.% based on the dried support material.

A particularly preferred method for the production of an isomerization catalyst is presented in U.S. Pat. No. 2,999,074. The carrier material and the platinum group component are composited and the resulting material is mildly calcined. This calcination is normally carried out under carefully controlled conditions to remove physically absorbed solvents such as water but to retain some chemically combined hydroxyl groups on the surface of the catalyst. Temperatures ranging from 350° to about 700° C. are usually satisfactory. The calcined composite is then reacted with a metal halide of the Friedel-Crafts type. Suitable metal halides include aluminum chloride, aluminum bromide, ferric chloride and zinc chloride, etc. Of these, aluminum chloride is particularly preferred.

Other recently developed isomerization catalysts including those of a bimetallic or trimetallic nature may be used in the process. An example of this is the catalytic composite comprising a platinum group component, a germanium component, and a Friedel-Crafts metal halide component shown in U.S. Pat. No. 3,649,704. In U.S. Pat. No. 3,652,697, there is disclosed a trimetallic catalyst comprising a platinum group component, a germanium component, a rhenium component and a Friedel-Crafts metal halide component.

The net hydrocarbon effluent of the isomerization zone is a mixture of isobutane and normal butane. This stream should contain 50 mole percent isobutane. Preferably this stream comprises 55 or 60 mole percent isobutane. The isomerization zone effluent and the isobutane-rich overhead stream of the deisobutanizer (second process stream) are both passed into a butane dehydrogenation zone. This zone will contain a reaction zone and associated auxiliary process equipment. The dehydrogenation zone contains at least one fractionation column. This column is designed and operated to eliminate all ethane and lighter boiling components from the net dehydrogenation zone effluent stream. It may also separate some and possibly all of the propylene into the light ends stream removed from this zone. The removal of ethane is necessary since the carryover of this light material into an HF alkylation zone will cause a loss of HF in the resultant net overhead vapor of the second fractionation zone. If a different alkylation catalyst is used, the presence of ethane in the alkylation zone feed stream may be acceptable. The propylene may result from the dehydrogenation of propane present in the feed stream to the process or from the cracking of butanes in the production of the light ends removed from this zone. This reaction zone preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction zone. A detailed description of moving bed reactors of this type may be obtained by reference to U.S. Pat. Nos. 3,647,680; 3,652,231; 3,706,536; 3,785,963; 3,825,116; 3,839,196; 3,839,197; 3,854,887 and 3,856,662.

The particular dehydrogenation conditions employed within the reaction zone may vary depending on such factors as the catalyst activity, feed carbon number and the desired conversion. The reaction zone conditions normally employed for butane dehydrogenation include a temperature of from about 500° to 700° C., a pressure of from 0.5 to about 10 atmospheres and a liquid hourly space velocity of about 1 to 20. The preferred operating temperature will be within the range of from about 550° to 650° C., and the preferred operating pressure is about 0.5 to 2 atmospheres.

The preferred butane dehydrogenation catalyst is comprised of a platinum group component, a tin component and an alkali metal component with a porous inorganic carrier material. Other catalytic compositions may be used within this zone if desired.

It is preferred that the porous carrier material is an absorptive high surface area support having a surface area of about 25 to about 500 m²/g. The porous carrier material should be relatively refractory to the conditions utilized in the reaction zone and may be chosen from those carrier materials which have traditionally been utilized in dual-function hydrocarbon conversion catalysts. A porous carrier material may therefore be chosen from an activated carbon, coke or charcoal, silica or silica gel, clays and silicates including those synthetically prepared and naturally occurring which may or may not be acid-treated, as for example attapulgus clay, diatomaceous earth, kieselguhr, bauxite; refractory inorganic oxides such as alumina, titanium dioxide, zirconium dioxides, magnesia, silica-alumina, alumina-boria, etc.; crystalline aluminosilicates such as naturally occurring or synthetically prepared mordenite or a combination of one or more of these materials. The preferred porous carrier material is a refractory inorganic oxide with the best results being obtained with an alumina carrier material. The crystalline alumina, such as gamma alumina, give the best results. In general, the preferred catalysts will have a gamma alumina carrier which is in the form of spherical particles having a relatively small diameter on the order of about 1/16-inch.

The preferred alumina carrier material may be prepared in any suitable manner. For example, the alumina carrier may be prepared by adding a suitable alkaline reagent, such as ammonium hydroxide to a salt of alumina such as aluminum chloride in an amount to form an aluminum hydroxide gel which upon drying and calcining, is converted to alumina. It is particularly preferred that alumina spheres are manufactured by the well-known oil drop method which comprises forming an alumina hydrosol by the techniques taught in the art, and preferably by reacting aluminum metal with hydrochloric acid, and combining the hydrosol with a suitable gelling agent. The resultant mixture is dropped into an oil bath maintained at elevated temperatures. The droplets remain in the oil bath until they set and form hydrogel spheres. The spheres are then continuously withdrawn from the oil bath and are normally subjected to specific aging treatments in oil and an ammoniacal solution to further improve their physical characteristics. The resulting pellets are then washed and dried at relatively low temperatures of about 150° to about 200° C. and calcined at a temperature of about 450° to about 700° C. for a period of about 1 to about 20 hours. See the teachings of U.S. Pat. Nos. 2,620,314 and 4,250,058 for additional details on the preparation of the base material by the oil dropping method.

The preferred dehydrogenation catalyst also contains a platinum group component. Of the platinum group metals, which include palladium, rhodium, ruthenium, osmium and iridium, the use of platinum is preferred with palladium being the next preferred metal. The platinum group components may exist within the final catalyst composite as a compound such as an oxide, sulfide, halide, oxysulfide, etc., or as an elemental metal or in combination with one or more other ingredients of the catalyst. It is believed that best results are obtained when substantially all the platinum group component exists in the elemental state. The platinum group component generally comprises from about 0.01 to about 2 wt.% of the final catalytic composite, calculated on an elemental basis. It is preferred that the platinum content of the catalyst is between about 0.1 and 1.0 wt.%. The platinum group component may be incorporated into the catalytic composite in any suitable manner such as by coprecipitation or cogelation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinic or chloropalladic acid. An acid such as hydrogen chloride is generally added to the impregnation solution to aid in the distribution of the platinum group component throughout the carrier material.

The tin component of the preferred catalyst should constitute about 0.01 to about 5 wt.% of the final composite, calculated on an elemental basis, although substantially higher amounts of tin may be utilized in some cases. Best results are often obtained with about 0.1 to about 1 wt% tin. It is preferred that the atomic ratio of tin to platinum is between 1:1 and about 6:1. The tin component may be incorporated into the catalytic composite in any suitable manner known to effectively disperse this component in a very uniform manner throughout the carrier material. Thus, the component may be added to the carrier by coprecipitation. A preferred method of incorporating the tin component involves coprecipitating it during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into the oil bath as previously described. The tin component may also be added through the utilization of a soluble, decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The preferred butane dehydrogenation catalyst contains less than 0.5 wt.% halogen and preferably less than 0.1 wt.% halogen. Residual amounts of any halogen, such as chlorine, at or below this concentration may be tolerated. The preferred catalyst does however contain an alkali metal component chosen from cesium, rubidium, potassium, sodium, and lithium. The preferred alkali metal is chosen from lithium and potassium. The concentration of the alkali metal may range from between 0.1 and 3.5 wt.% but is preferably between 0.2 and about 1.5 wt.% calculated on an elemental basis.

The entire net $C_3$-plus portion of the effluent of the dehydrogenation zone is passed into an alkylation zone. An isobutane-rich recycle stream removed from the second fractionation zone is preferably also passed into the alkylation zone. These two streams may be admixed prior to their passage into the alkylation zone. The dehydrogenation zone effluent stream may contain some propylene formed by the partial dehydrogenation of any propane present in the feed stream. This propylene is consumed in the same manner as the butylenes by reaction with the isobutane. The term "alkylation zone" is intended to indicate a sequence of processing equipment in which the entering reactants are contacted with an alkylation catalyst maintained at alkylation-promoting conditions including one or more reaction zones and the required equipment for the separation and recovery of the resultant alkylate from process streams within the alkylation zone. It is preferred that the alkylation zone contains no fractionation columns other than that used for catalyst regeneration.

The alkylation reaction is promoted by the presence of a mineral acid-catalyst such as hydrofluoric acid, sulfuric acid or phosphoric acid. These acids are maintained in a liquid phase containing a minimum of water to reduce corrosion problems. The maximum amount of water normally allowed in the acid is about 5 wt.%. When fresh acid is changed to a plant, it is normally very dry and contains about 0.5 wt.% water or less. The catalyst may also comprise a mixture of mineral acid and a Friedel-Crafts metal halide promoter such as aluminum chloride, aluminum bromide, boron trifluoride and other proton donors.

Alkylation conditions in general include a pressure sufficient to maintain the hydrocarbons and acid in a liquid phase, with a general range being from about 20 to about 500 psig, and a more preferred range being from 100 to about 250 psig. It is preferred that the pressure within the reactant-catalyst contacting vessel is approximately 150 psig and essentially "floats" on the pressure maintained in the downstream second fractionation zone. Although the alkylation rection may be performed at temperatures from below $-18°$ to about 90° C., it is preferred to operate the commercially prevalent isoparaffin-olefin alkylation process in the range of from about 10° to about 60° C., with 32° C. being a representative and particularly preferred operating temperature.

Typical operating conditions in the alkylation zone include a high ratio of the concentration of the paraffinic or other alkylatable material to the concentration of the olefinic material in order to produce a high quality alkylate by encouraging monoalkylation instead of polymerization. A broad range of this ratio is from about 6 to about 20 with a preferred operating range being from 8 to 12. If there is a shortage of isobutane in the alkylation zone, a portion of the deisobutanizer overhead stream may be passed directly into the alkylation zone. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.5:1, but it is preferred that the subject process is operated at an acid to hydrocarbon ratio of about 2:1.

There are a great number of olefin-isoparaffin alkylation processes known to those skilled in the art. The great majority of these processes will operate within the range of alkylation conditions set out above. They could however have substantial differences in equipment and flow paths used in performing the alkylation. These variations are attempts to obtain optimum quality alkylate by varying the method of contacting the monoolefin with the isoparaffin. Since this reaction occurs very rapidly, and also because hydrofluoric acid will catalyze the polymerization of the monoolefin, the standard alkylation methods consists of either first admixing acid-free streams of olefin and isoparaffin to form a reactant mixture which is then admixed with the hydrofluoric acid, or an acid-free olefin stream is mixed with an acid-containing isoparaffin stream. In either case, a large number of ventures or mixing nozzles are normally utilized to quickly disperse the olefin-containing stream into the acid-containing stream.

The resulting alkylation reaction is very exothermic and it is therefore necessary to provide means to remove the heat of reaction. This is normally done either by providing indirect heat-exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid phase is removed for recirculation, and the recirculated acid may be cooled to remove the heat of reaction. The hydrocarbon phase removed from the mixer settler is passed into the second fractionation column. This hydrocarbon phase will comprise mainly alkylate and the excess isoparaffin which was fed to the alkylation zone.

Some processes do not utilize a soak zone at all and still others contact the separated hydrocarbon phase with a regenerated high strength acid stream to aid in defluorination. Further details on the design and operation of reaction vessels, the overall operation of the alkylation step, the regeneration of the preferred HF catalyst, etc., may be obtained by reference to the previously cited references.

The net hydrocarbonaceous effluent stream of the alkylation zone is passed into the second fractionation column. This column is similar to that normally referred to as the isostripper column of HF catalyst motor fuel alkylation units. The isostripper covers the $C_8$ alkylate and other $C_5$-plus hydrocarbons as a net bottoms stream removed as the product of the process. When HF is used as the alkylation catalyst, the bottoms stream contains a small amount of isopentane produced in the alkylation zone. Some propane is also produced in the alkylation zone in this instance. As previously described, sidecut streams rich in isobutane and normal butane are also removed from the second fractionation column by recycling. If an acid catalyst, such as FH, is utilized in the alkylation zone, fluoride compounds will normally be present in any normal butane recycle stream. This stream should be passed through a fluoride removal zone comprising an alumina treater and a caustic contacting zone when the fluoride compounds will be detrimental to the isomerization catalyst. This is often the case with chloride-promoted isomerization catalysts. Such treatment is required with the preferred isomerization catalyst.

One embodiment of the inventive concept may be characterized as a hydrocarbon conversion process which comprises the steps of separating a feed stream which comprises a mixture of isobutane and normal butane into a first process stream which is rich in normal butane and a second process stream which is rich in isobutane in a first fractionation column, with the first process stream being withdrawn from the first fractionation column at an upper first intermediate point; passing the first process stream through an isomerization zone operated at butane isomerization conditions and thereby producing an isomerization zone effluent stream which comprises 50 mole percent isobutane; admixing the isomerization zone effluent stream and the second process stream to form a third process stream which comprises 70 mole percent isobutane; passing the third process stream through a dehydrogenation zone operated at butane dehydrogenation conditions and thereby producing a dehydrogenation zone effluent stream which comprises normal butane, isobutane, normal butanes and isobutylene; passing the dehydrogenation zone effluent stream and a hereinafter characterized third process stream into an HF alkylation zone operated at alkylation-promoting conditions and thereby producing an alkylation zone effluent stream which comprises normal butane, isobutane, isopentane and $C_8$ branched-chain hydrocarbons; separating the alkylation zone effluent stream in a second fractionation column into a first bottoms stream which is rich in $C_8$ branched-chain hydrocarbons, a lower sidecut stream which is rich in normal butane and comprises $C_8$ branched-chain hydrocarbons and an upper sidecut stream which is rich is isobutane; passing the lower sidecut stream into the first fractionation column at a lower second intermediate point; passing the upper sidecut stream into the alkylation zone as the previously referred to third process stream; and withdrawing a second bottoms stream comprising $C_8$ branched-chain hydrocarbons from the first fractionation column.

In order to ensure a complete understanding of the subject integrated process, a projected rough material balance of a processing unit having an overall flow similar to that shown in the drawing is given below. The line numbers designated in the Table correspond to lines on the Drawing. The relatively small light ends and hydrogen flows are not given. The material balance is for a unit in which propylene produced in the dehydrogenation zone is removed from the process as part of the light ends stream removed from this zone. All quantities are given in metric tons per stream day.

| Line | 1 | 3 | 4 | 6 | 9 | 13 | 15 | 16 | 17 | 19 |
|---|---|---|---|---|---|---|---|---|---|---|
| propane | 2.7 | 2.7 | — | — | 4.68 | 4.68 | 4.68 | — | — | — |
| butylene | — | — | — | — | 190.9 | — | — | — | — | — |
| $C_4$ diolefins | — | — | — | — | 19.4 | — | — | — | — | — |
| i-butane | 107.6 | 91.9 | 29.4 | 254.2 | 218.2 | 13.9 | 0.3 | 7.74 | — | 13.5 |
| n-butane | 339.8 | 22.0 | 482.6 | 254.2 | 185.1 | 18.9 | — | 7.11 | 16.2 | 181.3 |
| i-pentane | — | — | — | — | — | 10.4 | — | 376.7 | 3.1 | 3.1 |
| $C_6+$ | — | — | — | — | — | 380.0 | — | — | 3.1 | 3.1 |

I claim as my invention:

1. A hydrocarbon conversion process which comprises the steps of:
   (a) separating a feed stream which comprises a mixture of isobutane and normal butane into a first process stream which is rich in normal butane and a second process stream which is rich in isobutane in a first fractionation zone, with the first process stream being withdrawn from the first fractionation zone at a first intermediate point;
   (b) passing the first process stream through an isomerization zone operated at butane isomerization conditions and thereby producing an isomerization zone effluent stream which comprises a mixture of isobutane and normal butane having at least 50 mole percent isobutane;
   (c) passing the isomerization zone effluent stream and the second process stream, which if combined would contain less than 40 mole percent normal butane and more than 70 mole percent isobutane, through a dehydrogenation zone operated at butane dehydrogenation conditions and thereby producing a dehydrogenation zone effluent stream which comprises normal butane, isobutane, normal butenes and isobutylene;
   (d) passing the dehydrogenation zone effluent stream, wherein all of said hydrocarbons have passed through said dehydrogenation zone at least once, into an alkylation zone operated at alkylation-promoting conditions and thereby producing an alkylation zone effluent stream which comprises normal butane, isobutane and $C_8$ branched-chain hydrocarbons;
   (e) separating the alkylation zone effluent stream in a second fractionation zone and thereby producing a first bottoms stream which is rich in C<sub>8</sub> branched-chain hydrocarbons and a lower sidecut stream which is rich in normal butane and comprises $C_8$ branched-chain hydrocarbons;

(f) passing the lower sidecut stream into the first fractionation zone at a lower second intermediate point;

(g) withdrawing a second bottoms stream comprising $C_8$ branched-chain hydrocarbons from the first fractionation zone; and, (h) combining the first and the second bottoms streams and producing a product stream which is rich in $C_8$ branched-chain hydrocarbons.

2. The process of claim 1 further characterized in that an upper sidecut stream which is rich in isobutane is removed from the second fractionation zone and passed into the alkylation zone.

3. The process of claim 1 further characterized in that the second process stream is removed from the first fractionation zone as a net overhead stream.

4. The process of claim 3 further characterized in that a net overhead stream comprising propane and isobutane is removed from the second fractionation zone.

5. The process of claim 4 further characterized in that liquid phase HF is utilized as a catalyst within the alkylation zone.

6. The process of claim 5 further characterized in that the butane dehydrogenation zone contains a catalytic composite containing platinum, tin and an alkali metal component.

7. The process of claim 6 further characterized in that the butane isomerization zone contains a catalytic composite containing a platinum group metal and a Friedel-Crafts metal halide.

8. A hydrocarbon conversion process which comprises the steps of:

(a) separating a feed stream which comprises a mixture of isobutane and normal butane into a first process stream which is rich in normal butane and a second process stream which is rich in isobutane in a first fractionation column, with the first process stream being withdrawn from the first fractionation column at an upper first intermediate point;

(b) passing the first process stream through an isomerization zone operated at butane isomerization conditions and thereby producing an isomerization zone effluent stream which comprises 50 mole percent isobutane;

(c) admixing the isomerization zone effluent stream and the second process stream to form a third process stream which comprises 70 mole percent isobutane;

(d) passing the third process stream through a dehydrogenation zone operated at butane dehydrogenation conditions and thereby producing a dehydrogenation zone effluent stream which comprises normal butane, isobutane, normal butenes and isobutylene;

(e) passing the dehydrogenation zone effluent stream, wherein all of said hydrocarbons have passed through said dehydrogenation zone at least one, and a hereinafter characterized fourth process stream into an HF alkylation zone operated at alkylation-promoting conditions and thereby producing an alkylation zone effluent stream which comprises normal butane, isobutane, isopentane and $C_8$ branched-chain hydrocarbons;

(f) separating the alkylation zone effluent stream in a second fractionation column into a first bottoms stream which is rich in $C_8$ branched-chain hydrocarbons, a lower sidecut stream which is rich in normal butane and comprises $C_8$ branched-chain hydrocarbons and an upper sidecut stream which is rich in isobutane;

(g) passing the lower sidecut stream into the first fractionation column at a lower second intermediate point;

(h) passing the upper sidecut stream into the alkylation zone as the previously referred to fourth process stream;

(i) withdrawing a second bottoms stream comprising $C_8$ branched-chain hydrocarbons from the first fractionation column; and, (j) recovering said first bottoms stream as the product stream of said hydrocarbon conversion process.

9. The process of claim 8 further characterized in that the catalyst employed in the dehydrogenation zone comprises a platinum group component, a tin component and an alkali metal chosen from lithium or potassium on a porous inorganic oxide support.

10. The process of claim 8 further characterized in that the third process stream comprises 75 mole percent isobutane.

11. The process of claim 8 further characterized in that said first bottoms stream recovered as product is admixed with said second bottoms removed from said first fractionation column.

* * * * *